United States Patent
Chang

(10) Patent No.: US 8,660,630 B2
(45) Date of Patent: *Feb. 25, 2014

(54) ECG LEADS SYSTEM FOR NEWBORN ECG SCREENING

(75) Inventor: Ruey-Kang Chang, Diamond Bar, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 275 days.

This patent is subject to a terminal disclaimer.

(21) Appl. No.: 13/165,467

(22) Filed: Jun. 21, 2011

(65) Prior Publication Data

US 2011/0270100 A1 Nov. 3, 2011

Related U.S. Application Data

(63) Continuation-in-part of application No. 11/951,083, filed on Dec. 5, 2007, now Pat. No. 8,369,924.

(60) Provisional application No. 60/882,122, filed on Dec. 27, 2006.

(51) Int. Cl.
*A61B 5/0408* (2006.01)

(52) U.S. Cl.
USPC .......... 600/386; 600/391; 600/392; 600/393; 600/509

(58) Field of Classification Search
USPC .......................... 600/382, 386, 388–393, 509
See application file for complete search history.

(56) References Cited

U.S. PATENT DOCUMENTS

| 3,888,240 A | 6/1975 | Reinhold, Jr. et al. |
| 4,233,987 A | 11/1980 | Feingold |

(Continued)

FOREIGN PATENT DOCUMENTS

| GB | 2149918 | 6/1985 |
| WO | WO-99/40844 | 8/1999 |

(Continued)

OTHER PUBLICATIONS

La Biomed, Non final office action dated Jun. 24, 2011 for U.S. Appl. No. 11/951,083.

(Continued)

*Primary Examiner* — Lee S Cohen
(74) *Attorney, Agent, or Firm* — W. Thomas Babbitt; Blakely Sokoloff Taylor & Zafman LLP

(57) ABSTRACT

An apparatus including a chest strip comprising a plurality of precordial and limb leads for an electrocardiogram (ECG) and an ECG data recorder coupled to the chest strip, wherein the ECG data recorder configured to receive signals from the leads. An apparatus including a chest strip comprising a plurality of precordial leads positioned to correspond with desired lead placement for an electrocardiogram (ECG) and an ECG data recorder; a plurality of limb leads coupled to the chest strip, wherein the ECG data recorder is coupled to plurality of precordial leads and the plurality of limb leads and configured to receive electrocardiogram data generated by the plurality of precordial leads and the plurality of limb leads. A method including coupling a chest strip including precordial leads and a data recorder to a newborn, the data recorder configured to receive electrocardiogram data from the precordial leads; and transmitting electrocardiogram data from the data recorder.

18 Claims, 7 Drawing Sheets

(56) References Cited

U.S. PATENT DOCUMENTS

| | | | |
|---|---|---|---|
| 4,498,480 | A | 2/1985 | Mortensen |
| 4,608,987 | A | 9/1986 | Mills |
| 4,957,109 | A | 9/1990 | Groeger et al. |
| 5,184,620 | A | 2/1993 | Cudahy et al. |
| 5,224,479 | A | 7/1993 | Sekine |
| 5,307,818 | A * | 5/1994 | Segalowitz ............... 600/509 |
| 5,341,806 | A | 8/1994 | Gadsby et al. |
| 5,445,149 | A | 8/1995 | Rotolo et al. |
| 5,782,238 | A | 7/1998 | Beitler |
| 5,813,979 | A | 9/1998 | Wolfer |
| 5,865,736 | A | 2/1999 | Baker, Jr. et al. |
| 5,868,671 | A | 2/1999 | Mahoney |
| 6,128,521 | A | 10/2000 | Marro et al. |
| 6,295,463 | B1 | 9/2001 | Stenzler |
| 6,334,065 | B1 | 12/2001 | Al-Ali et al. |
| 6,341,229 | B1 | 1/2002 | Akiva |
| 6,415,169 | B1 | 7/2002 | Kornrumpf et al. |
| 6,453,186 | B1 | 9/2002 | Lovejoy et al. |
| 6,611,705 | B2 | 8/2003 | Hopman et al. |
| 6,719,705 | B2 | 4/2004 | Mills |
| 6,775,566 | B2 * | 8/2004 | Nissila ............... 600/382 |
| 6,847,836 | B1 | 1/2005 | Sujdak |
| 6,909,912 | B2 | 6/2005 | Melker |
| 7,444,177 | B2 | 10/2008 | Nazeri |
| 7,904,133 | B2 * | 3/2011 | Gehman et al. ............. 600/391 |
| 8,369,924 | B1 * | 2/2013 | Chang ............... 600/386 |
| 2002/0124295 | A1 | 9/2002 | Fenwick et al. |
| 2002/0133069 | A1 | 9/2002 | Roberts |
| 2003/0092996 | A1 | 5/2003 | Lowe et al. |
| 2006/0030782 | A1 | 2/2006 | Shennib |
| 2006/0047213 | A1 | 3/2006 | Gavriely et al. |
| 2006/0047215 | A1 | 3/2006 | Newman et al. |
| 2006/0069320 | A1 | 3/2006 | Wolff et al. |
| 2006/0149324 | A1 | 7/2006 | Mann et al. |
| 2006/0224072 | A1 | 10/2006 | Shennib |
| 2006/0247548 | A1 | 11/2006 | Sarkar et al. |
| 2006/0253007 | A1 | 11/2006 | Cheng et al. |
| 2006/0253044 | A1 | 11/2006 | Zhang et al. |
| 2007/0027388 | A1 * | 2/2007 | Chou ............... 600/393 |
| 2007/0142715 | A1 | 6/2007 | Banet et al. |
| 2007/0149887 | A1 * | 6/2007 | Hwang et al. ............. 600/509 |
| 2007/0276273 | A1 * | 11/2007 | Watson, Jr ............. 600/511 |
| 2008/0177168 | A1 | 7/2008 | Callahan et al. |
| 2009/0076364 | A1 * | 3/2009 | Libbus et al. ............. 600/391 |

FOREIGN PATENT DOCUMENTS

| | | |
|---|---|---|
| WO | WO-0193756 | 12/2001 |
| WO | WO-0222010 | 3/2002 |
| WO | WO-03011132 | 2/2003 |

OTHER PUBLICATIONS

Los Angeles Biomedical Research Institute et al., PCT International Search Report and Written Opinion mailed Nov. 11, 2007, PCT/US2007/015451, (Nov. 22, 2007).

Ackerman, M. J., et al., "Postmortem Molecular Analysis of SCN5A Defects in Sudden Infant Death Syndrome", JAMA, vol. 286, No. 18, (Nov. 14, 2001), pp. 2264-2269.

Arlettaz, et al., "The contribution of pulse oximetry to the early detection of congenital heart disease in newborns", Eur J Pediatr, 165, (2006), 94-98.

Arnestad, M., et al., "Prevalence of Long-QT Syndrome Gene Variants in Sudden Infant Death Syndrome", Circulation, Issue 115, (Jan. 8, 2007), pp. 361-367.

Bakr, et al., "Combining pulse oximetry and clinical examination in screening for congenital heart disease", Pediatric Cardiology, 26, (2005), 832-835.

Barclay, MD, L., "Some Cardiologists Recommend Routine ECG Screening of Newborns", Medscape Medical News, retrieved via Internet: <http://www.medscape.com/viewarticle/540941>, (Jul. 14, 2006), 3 pages.

Geggel, "Conditions leading to pediatric cardiology consultation in a tertiary academic hospital", Pediatrics, 114:4, (2004), e409-17.

Hoke, et al., "Oxygen saturation as a screening test for critical congenital heart disease: a preliminary study", Pediatric Cardiology, 23, (2002), 403-409.

Knowles, et al., "Newborn screening for congenital heart defects: a systematic review and cost-effectiveness analysis", Health Technology Assessment, 9:44, (Nov. 2005).

Koppel, et al., "Effectiveness of pulse oximetry screening for congenital heart disease in asymptomatic newborns", Pediatrics, 111:3, (Mar. 2003), 451-455.

La Biomed, Final office action dated Sep. 16, 2009 for U.S. Appl. No. 11/772,743.

Li, et al., "Will a handheld ultrasound scanner be applicable for screening for heart abnormalities in newborns and children?", J Am Soc Echocardiogr., 16:10, (2003), 1007-14.

Quaglini, S. , et al., "Cost-effectiveness of neonatal ECG screening for the long QT syndrome", European Heart Journal, vol. 27, (2006), pp. 1824-1832.

Reich, et al., "The use of pulse oximetry to detect congenital heart disease", J Pediatr, 142, (2003), 268-272.

Richmond, et al., "Routine pulse oximetry in the asymptomatic newborn", Arch Dis Child Fetal Neonatal Ed., 87, (2002), F83-8.

Rosati, et al., "Indications and limitations for a neonatal pulse oximetry screening of critical congenital heart disease", J. Perinat. Med., 33, (2005), 455-457.

Schwartz, MD, P. J., "Newborn ECG Screening to Prevent Sudden Cardiac Death", Hearth Rhythm, vol. 3, Issue 11, retrived via Internet: <http://sciencedirect.com>, (Nov. 2006), 1353-1355.

Schwartz, MD, P. J., et al., "Prolongation of the QT Interval and the Sudden Infant Death Syndrome", The New England Journal of Medicine, vol. 338, No. 24, (Jun. 11, 1998), pp. 1709-1714.

Van Langen, I. M., et al., "Newborn screen to prevent sudden cardiac death?", Heart Rhythm, vol. 3, Issue 11, (Nov. 2006), pp. 1356-1359.

Wever, MD, Eric F., et al., "Sudden Death in Patients Without Structural Heart Disease", Journal of the American Colleage of Cardiology, vol. 43, No. 7, (Apr. 7, 2004), pp. 1137-1144.

Wilson, M. , "ECG Screening for All Newborns Would Identify Life-Threatening Heart Condition", Medical News Today, retrieved via Internet: <http://medicalnewstoday.com/medicalnews>, (Jul. 16, 2006), 2 pp.

Wilson, M., "Routine ECGs for newborns would identify life-threatening heart condition", Innovations Report, retrieved via Internet: <http://www.innovations-report.com>, (Jul. 13, 2006), 3 pages.

Wren, et al., "Presentation of congenital heart disease in infancy: implications for routine examination", Arch Dis Child Fetal Neonatal Ed., 80, (1999), F49-53.

Los Angeles Biomedical Research, Non-Final Office Action mailed Feb. 22, 2012 for U.S. Appl. No. 11/951,083.

Los Angeles Biomedical Research, Final Office Action mailed Oct. 12, 2011 for U.S. Appl. No. 11/951,083.

Los Angeles Biomedical Research, Final Office Action mailed Jul. 23, 2012 for U.S. Appl. No. 11/951,083.

* cited by examiner

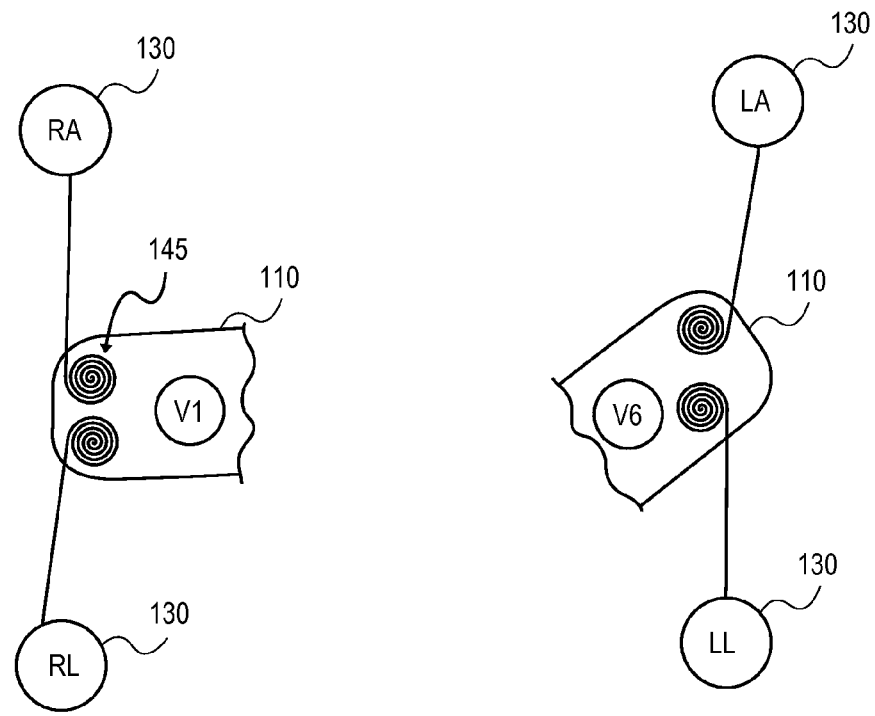
FIG. 3
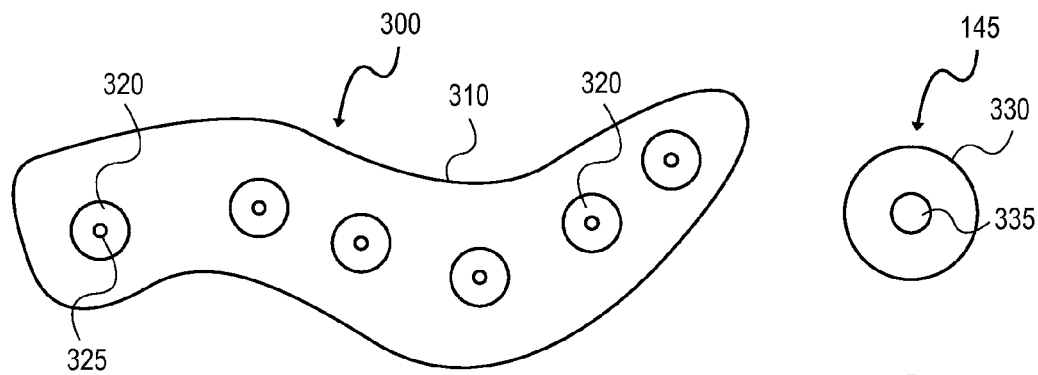
FIG. 4
FIG. 5

ECG LEADS SYSTEM FOR NEWBORN ECG SCREENING

CROSS-REFERENCE TO RELATED APPLICATION

This application is a continuation-in-part of U.S. patent application Ser. No. 11/951,083, filed Dec. 5, 2007, now U.S. Pat. No. 8,369,924, which claims the benefit of the earlier filing date of co-pending U.S. Provisional Patent Application No. 60/882,122, filed Dec. 27, 2006, and incorporated herein by reference.

FIELD

Neonatal electrocardiogram screening.

BACKGROUND

Long QT syndrome (LQTS) is a genetic disease characterized by an abnormally prolonged QT interval in the electrocardiogram (ECG) waveform. LQTS is a leading cause of sudden cardiac death in the young. When infants with undiagnosed LQTS die, their sudden deaths are often labeled as sudden infant death syndrome (SIDS) because no apparent cause of death could be found by autopsy. Using post-mortem genetic analysis, researchers have found that more than 10% of SIDS cases are actually due to undiagnosed LQTS. LQTS can be diagnosed by a routine 12-lead ECG. Once diagnosed, the treatments for LQTS, including beta-blocker therapy and implantable cardioverter defibrillator (ICD), are very effective in preventing cardiac arrhythmia and sudden death. Therefore, some European countries are considering the possibility of introducing neonatal (days 15-25) ECG screening as part of their National Health Services. Among the European countries, Italian Ministry of Health funded an electrocardiogram (ECG) screening program on over 50,000 babies to assess the feasibility and outcomes of a nationwide neonatal ECG screening. The program has been tremendously successful, and such success has generated enthusiasm toward implementation of a nationwide screening program from many European nations and the United States.

Since the proposed screening ECGs are targeted at two to four weeks of life, the screenings for LQTS proposed will likely have to be done at a pediatrician's office or at home. Most nurses or nurse's assistants are not trained to perform newborn ECGs. A regular ECG machine has 10 long cables which often tangle among themselves. When conducting an ECG test, the operator needs to place 10 electrodes (stickers) on the patient and match the cables with each respective electrode on the patient. This process of untangling the cables, placing electrodes, and matching the cables and electrodes takes skill and time.

Performing an ECG on a newborn is challenging and often takes up to 20 minutes or more. Placing the leads on a newborn is difficult because of limited space on the torso and the babies are not cooperative. Furthermore, performing an ECG on a newborn using the current complicated leads system by inexperienced nurses is prone to error, such as wrong leads placement, artifacts, and inadequate ECG signal acquisition.

To solve the issues with improper leads placement and tangling of cables, prior inventions have used pre-positioned leads or one-piece design. U.S. Pat. Nos. 4,608,987 and 5,224,479 describe a vest containing pre-positioned leads, which is cumbersome to use in babies and requires a large area of skin contact when worn. Chest strip designs have been proposed by U.S. Pat. Nos. 4,233,987, 5,184,620, and 5,868, 671. The limitations of these designs are that they are not designed for use in newborns and infants; and only three to six chest leads are typically provided (e.g., the strips lack limb leads) and therefore cannot be used for QT analysis. U.S. Pat. No. 6,847,836 proposes a one-piece chest pad design for use of ECG monitoring in the emergency room. The chest pad design is not specific for newborns and infants, and has a large skin contact area, which is an important limitation for use in babies because of their sensitive skin. Furthermore, the limb lead positions in the chest pad design of U.S. Pat. No. 6,847, 836 are not generally proper for accurate measurement of QT intervals on a 12-lead ECG. As a result, QT analysis using such a design and system is not generally accurate.

ECG is mostly performed in adults, especially elderly people. ECG on newborns used to be a rare practice. None of the current ECG machine or leads system is designed for use in newborns or infants. As many nations are considering implementing a nationwide newborn ECG screening program, there is an urgent need for a simple, quick and error-proof ECG leads system for newborns. The current design is an ECG leads system specifically designed for newborns to be used in pediatrician's office, hospital or even at home by parents for newborn screening.

SUMMARY

An ECG system designed for performing newborn ECG is disclosed. In one embodiment, the leads system includes a chest strip which contains precordial leads; retractable limb leads, wireless connector or cable and a leads adaptor. This system with simple, pre-positioned leads allows quick and accurate leads placement for conducting newborn ECG.

A method of performing an ECG using an ECG leads system is also disclosed. In one embodiment, the method may be used on a newborn infant to detect LQTS and minimize the risk for SIDS.

BRIEF DESCRIPTION OF THE DRAWINGS

FIG. 3 shows a schematic side view of two portions of the chest strip of the ECG leads system of FIG. 1 and shows retractable limb leads partially retracted.

FIG. 4 shows a schematic top view of a disposable electrode strip suitable for use with the chest strip of the ECG leads system of FIG. 1.

FIG. 5 shows a schematic top view of a disposable electrode lead suitable for use with limb leads of the ECG leads system of FIG. 1.

DETAILED DESCRIPTION

An ECG leads system for conduction of newborn ECG is described. In one embodiment, this ECG leads system connects directly with an ECG machine. In another embodiment, this ECG leads system includes an adapter that can connect to the cables of an ECG machine to allow the use with existing ECG machines already in hospitals or physician's offices.

Figure 1:
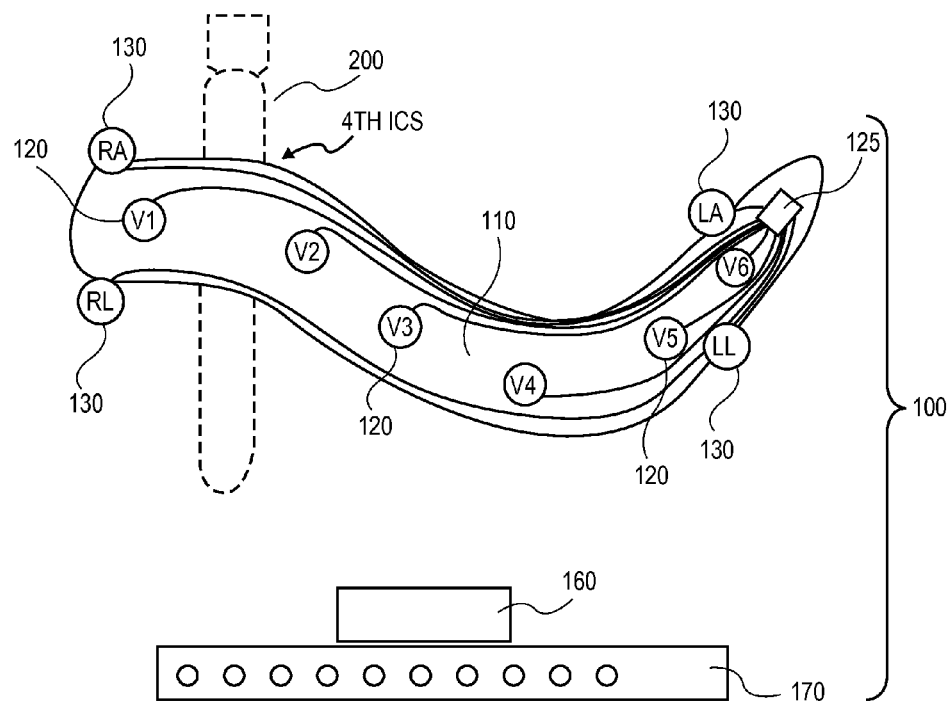
FIG. 1 illustrates a schematic view of an embodiment of an ECG leads system including a cross-sectional top view of a chest strip, and side views of a receiver and an adapter.

FIG. 1 illustrates an embodiment of an ECG system. In the illustrated embodiment, ECG system 100 includes the following components: chest strip 110 including a plurality of precordial leads 120 and transceiver 125; retractable limb leads 130; receiver 160; and adapter 170 to connect to an ECG machine. A cross-sectional top view of chest strip 110 is shown to illustrate precordial leads 120 and transceiver 125.

Figure 6:
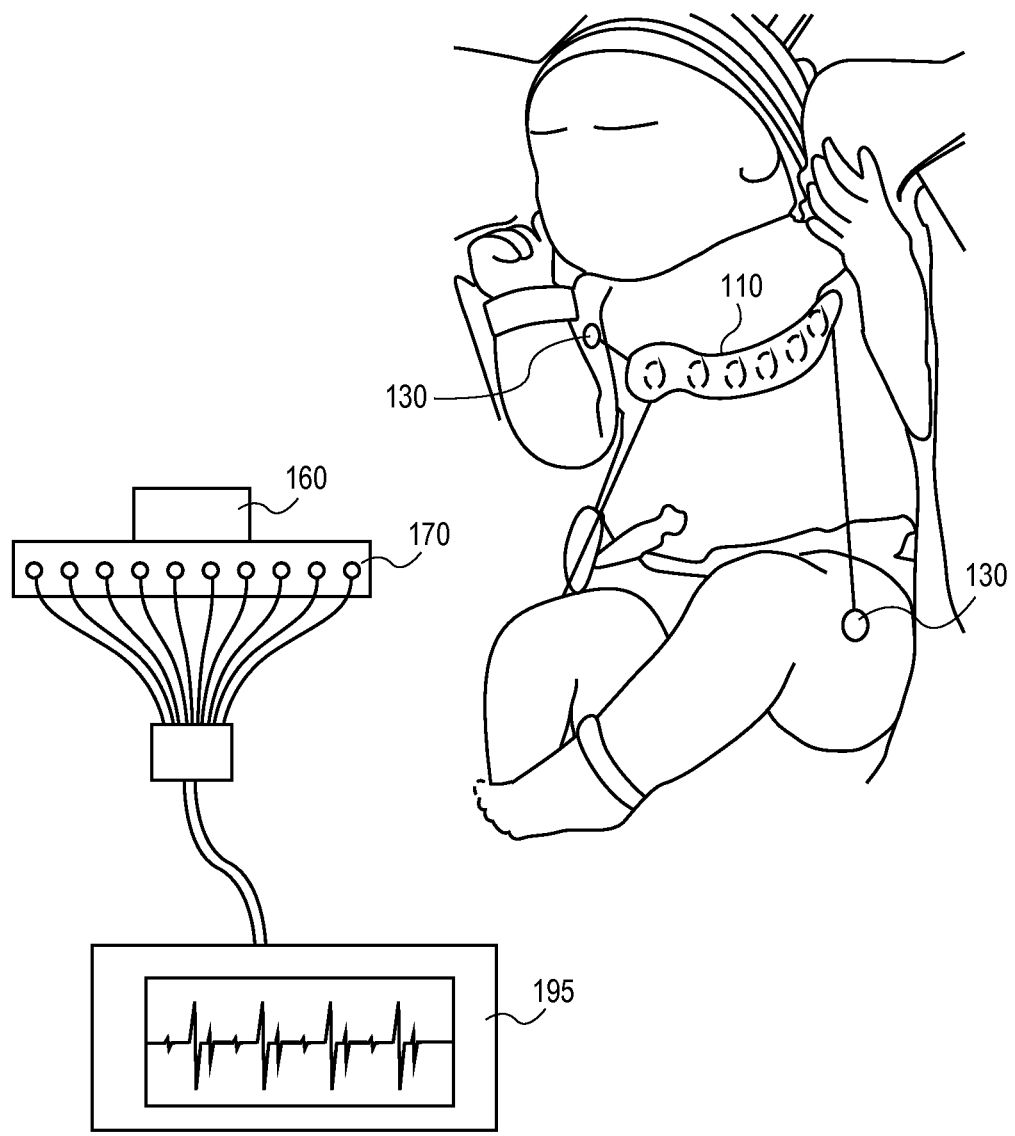
FIG. 6 shows a schematic view of the ECG leads system recording an ECG of a newborn.

In one embodiment, chest strip 110 is designed to embed six precordial leads 120 (V1, V2, V3, V4, V5, and V6). The chest strip is shaped in a way shown in FIG. 1 so that when placed on a newborn's chest, precordial leads 120 (V1 to V6) will be in proper positions for routine ECG leads placements. As shown in FIG. 1, the chest strip will be placed so that V1 will be in the $4^{th}$ intercostal space (ICS) on the right sternal border, and V2 will be in the $4^{th}$ ICS on the left sternal border. The $4^{th}$ ICS is at approximately the nipple line which is a convenient landmark for chest strip placement. Indicators for sternum 200 position are shown on the chest strip to assist the operator to position V1 and V2 at opposite sides of the sternum. The positions of V3 to V6 will also be placed properly and chest strip 110 will be shaped accordingly. V4 will be at $5^{th}$ ICS in the left mid-clavicular line; V3 will be half way between V2 and V4; V5 will be at the level of V4 in the left anterior auxiliary line, and V6 will be at the level of V4 in the left mid-auxiliary line. Because the chest sizes of newborns at three to five kilograms (kg) body weight do not vary widely, chest strip 110 may be one size that will fit all. In one embodiment, the width of the chest strip is 2 cm and length is 12 cm. In another embodiment, the dimensions are reduced to fit premature infants or infants with smaller chest sizes. FIG. 6 shows chest strip 110 applied to the chest of a newborn.

Figure 2:
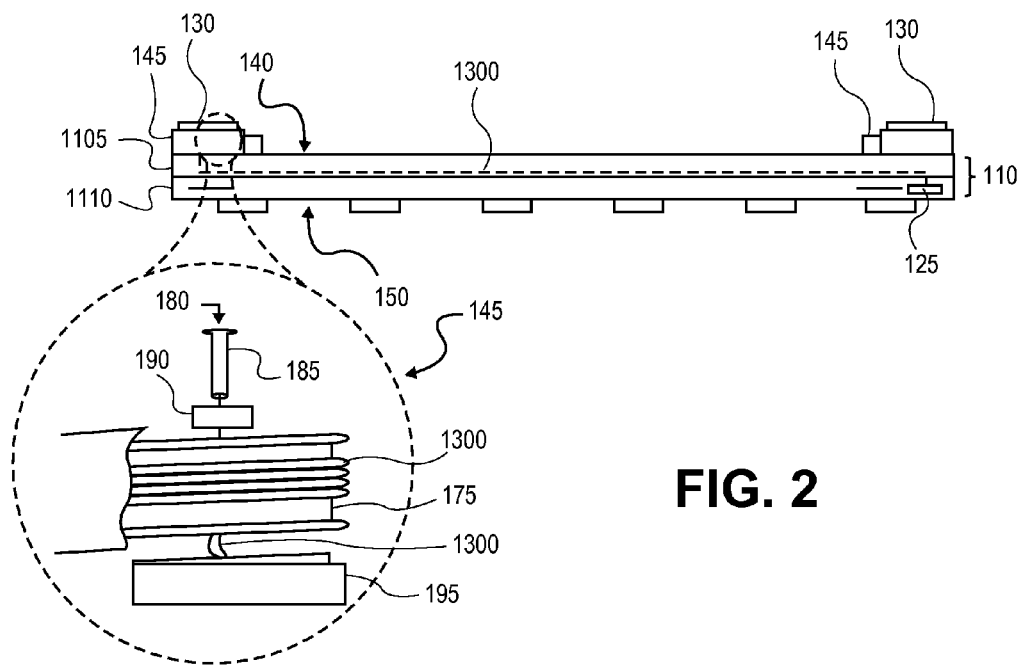
FIG. 2 shows a side view of the chest strip of FIG. 1.

In one embodiment, chest strip 110 is made of nonconductive, flexible material such as plastic, or natural or synthetic fabric. FIG. 2 shows a side view of an embodiment of chest strip 110. In this embodiment, chest strip 110 is made of two layers of material (material layer 1105 and material layer 1110). Chest strip 110 has surface 140 intended to face away from a newborn's skin when chest strip 110 is applied and surface 150 opposite surface 140 and having leads 150 exposed therethrough. Surface 140 of chest strip 110 is generally smooth with no exposed components. On opposite surface 150 of chest strip 110, six round shape precordial leads 120, each representatively 10 millimeters (mm) in diameter, are positioned in V1, V2, V3, V4, V5, and V6 locations. Precordial leads 120 are made of a conductive material such as silver. Each of the leads V1 to V6 connects to its own wire that connects to transceiver 125 or a cable (see FIG. 5 and the accompanying text). The wires are electrically insulated from one another so that there will be no interference among the leads. In the embodiment shown in FIG. 2, precordial leads 120 may be placed through layer 1110 with wires connected between the leads and transceiver 125. Layer 1105 lies on the wires and hides the wires in chest strip 110 (e.g., the wires are disposed between layer 1110 and layer 1105).

In one embodiment, ECG system 100 shown in FIG. 1 and FIG. 2 includes limb leads 130 connected to chest strip 110. Right limb leads 130, RA and RL, are located on the right end of chest strip 110 when the chest strip is applied to a newborn's chest (FIG. 1). Left limb leads 130, LA and LL, are located on the left end of chest strip 110 (FIG. 1). FIG. 6 shows limb leads 130 applied to a newborn.

In one embodiment, a wire extends between each limb lead 130 and transceiver 125, with a portion of each wire extending through chest strip 110 similar to the wires that connect the precordial leads 130 to transceiver 125. The wires are electrically insulated from one another and from the wires of precordial leads 120. As shown in FIG. 2, in one embodiment, the wires that connect limb leads 130 to transceiver 125 extend at each end from chest strip 110 into a respective hub 145 (shown illustratively on surface 140 of chest strip 110). Each hub 145 includes drum 175 on which, in this example, wire 1300 is wound. Drum 175 is rotatable on axis 180 defined by axle bolt or rivet 185 and bearing 190. Spring biased roller 195 is connected to wire 1300 interiorly of drum 175 and having a center axis co-axially aligned with axis 180, the roller functioning to exert a retract force continuously on wire 1300 even when the wire is uncoiled from drum 175 and hub 145. Wire 1300 is continuously biased toward a storage position in hub 145.

The wires connecting to limb leads 130 are self-retractable or are biased toward coiling the wires in respective hubs 145. A pulling force on a limb lead is required to uncoil a wire for a limb lead. Release of the pulling force returns the wire to a coiled configuration. In this manner, when not placed on a limb of a newborn, the leads are conveniently housed in respective hubs 145 to minimize wires tangling. When in use, after chest strip 110 is properly placed on the newborn, each of limb leads 130 can be pulled out to position in the proper places for the regular limb leads placement (FIG. 3 and FIG. 6). In one embodiment, the wires for upper limb leads (RA and LA) are five inches when fully uncoiled, and the wires for lower limb leads (RL and LL) are eight inches when fully uncoiled. The lengths of the limb leads wires will allow proper placement of limb leads 130. In one embodiment, a stop may be included on each wire when a lead is uncoiled and positioned. Such a stop may be as simple as a clip on the wire directly outside hub 145 or more elaborate such as an actuator connected to hub 145 to lock roller 195. When an ECG recording is finished, the operator will push the actuator to unlock roller 195 and allow a wire to retract back to hub 145 and return the lead into a stored position (FIG. 2).

Referring to precordial leads 120 and limb leads 130, in one embodiment, the leads are not placed directly on a newborn's skin. Instead, disposable electrodes are representatively used to ensure good skin contact and connection with the ECG leads. FIG. 4 shows a side view of disposable electrode 300 that is in a similar shape of chest strip 110 with six round-shaped ionically conductive hypoallergenic hydrogel adhesives 320 placed in similar positions of the V1, V2, V3, V4, V5 and V6 leads 120 on chest strip 110 (see FIG. 1). In one embodiment, each adhesive 320 is 16 millimeters (mm) in diameter, with electrically conductive button 325 (e.g., a stainless steel button) in the center on a first surface. A second surface of electrode 300 is covered by a removable plastic cover. Prior to applying chest strip 110 to a newborn's chest, an operator will place the disposable electrode 300 on the underside of chest strip 110 such that each button 325 in the center of each adhesive 320 is in proper contact with the electrically conductive (e.g., silver) center of leads 120 on the chest strip. Then the operator will remove the thin plastic cover of electrode 300 to expose an adhesive side of each adhesive 320 and apply electrode 300 and chest strip 110 on the newborn's chest. In one embodiment, the adhesive between electrode 300 and chest strip 110 is hypoallergenic hydrogel. In an embodiment where the adhesive is associated only with adhesive 320 rather than the entire chest strip, the contact with a newborn's skin is minimized.

FIG. 5 shows disposable electrode 305 that may be used with the limb leads 130. Electrode 305 includes round ionically conductive hypoallergenic hydrogel adhesive 330, 20 mm in diameter, with a conductive (e.g., stainless steel) button 335 in the center on one surface to contact a conductive portion of limb lead 130. A removable plastic cover may be placed over a second adhesive surface of adhesive 330. The cover will be removed prior to attaching the electrode on the newborn. In one embodiment, a hypoallergenic hydrogel is provided on the adhesive surface of each electrode 305 that will ensure good skin contact. After chest strip is placed properly on the chest, the operator will pull each individual limb leads out and clip or snap on a respective electrode 330.

As noted above, in one embodiment the wires from limb leads 130 (RA, RL, LA, LL) and precordial leads 120 (V1, V2, V3, V4, V5, V6) run through chest strip 110 individually and connect to transceiver 125. Transceiver 125 is, for example, a Bluetooth chip located at the left end of chest strip 110. In one embodiment, transceiver 125 is programmed to receive and transmit ECG signals from limb leads 130 and precordial leads 120. In the embodiment of ECG system 100 shown in FIG. 1, transceiver 125 wirelessly sends ECG signals received from the various leads to receiver 160, such as a Bluetooth chip. Receiver 160 then distributes the received signals to contact points of adaptor 170 (contact points corresponding to signals for six precordial leads V1, V2, V3, V4, V5, V6, and four limb leads RA, RL, LA, LL). Such signals may be transmitted from adaptor 170 by hard wiring a connection between the contact points and an ECG machine (see FIG. 6).

In one embodiment, adaptor 170 is designed to make ECG leads system 100 compatible with existing, commercially available ECG machines. In one embodiment, the contact points on adaptor 170 are the same as used on regular ECG electrodes, which allows the leads from commercial ECG machine to clip on or clamp on. FIG. 6 shows ECG system 100 connected to ECG machine 195 and illustrates an ECG signal displayed on ECG machine 195.

Figure 7:
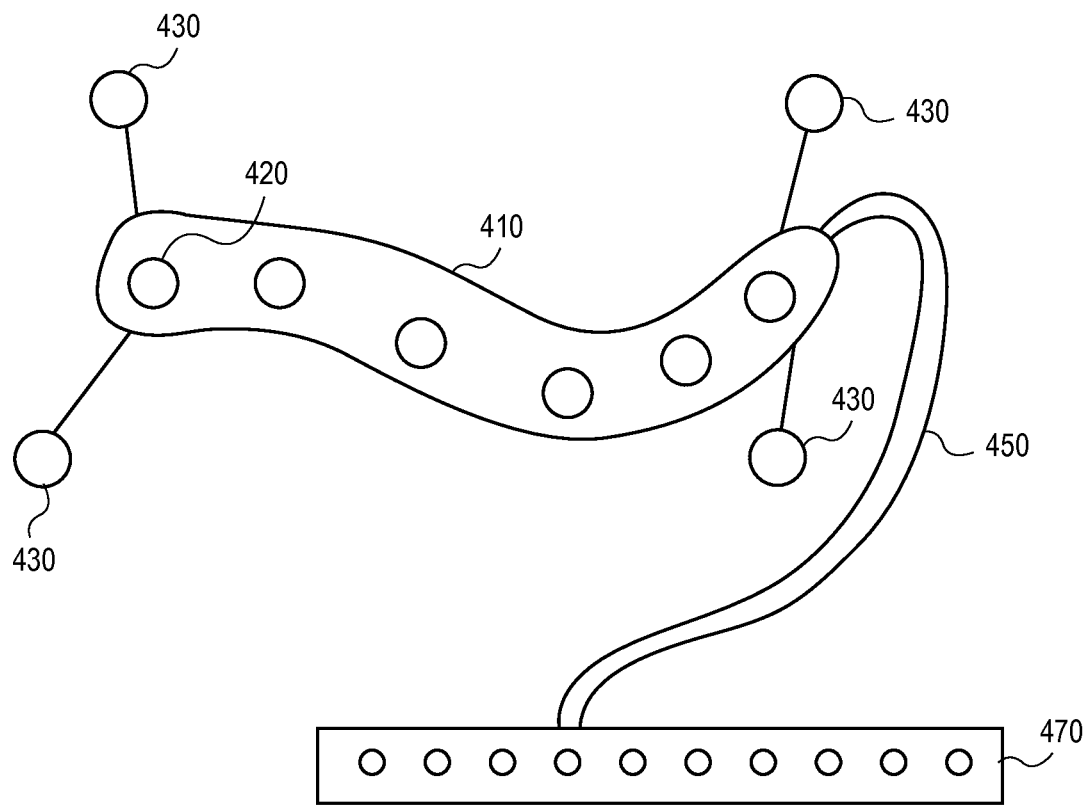
FIG. 7 shows a schematic side view of another embodiment of an ECG leads system including a chest strip, a cable, and an adapter.

FIG. 7 shows another embodiment of an ECG system where the connection between a chest strip and a leads adaptor uses wired cable instead of wireless technology. FIG. 7 shows chest strip 410 including precordial leads 420 (V1, V2, V3, V4, V5, V6). FIG. 7 also shows limb leads 430 (RA, RL, LA, LL) connected by individual wires to chest strip 410. The wires for precordial leads 420 and limb leads 430 extend into harness 450 which connects to adaptor 470. The signals at adaptor 470 may then be transferred (e.g., via wires) to an ECG machine. Alternatively, harness 450 may connect limb leads 430 and precordial leads 420 on chest strip 410 directly to an ECG machine without the use of adaptor 470. The wires inside harness 450 are electrically insulated from one another. A representative length of harness 450 is from one foot up to 12 feet depending on the needs.

Figure 8:
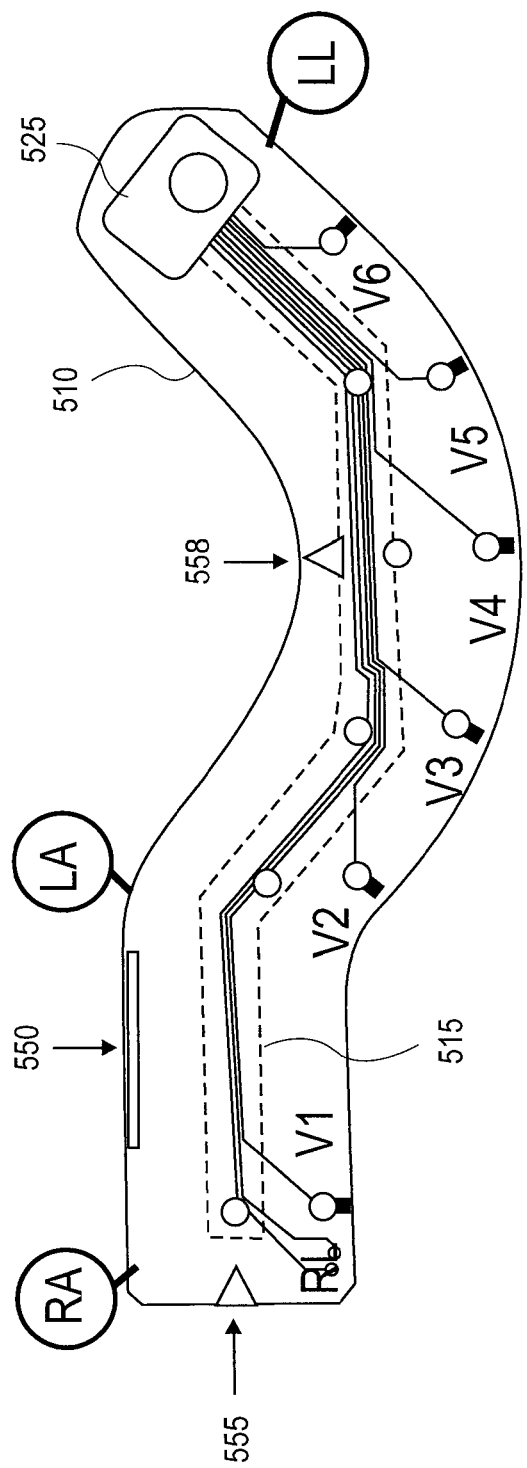
FIG. 8 shows a schematic top view of another embodiment of an ECG system including a chest strip and a data recorder.

FIG. 8 shows an embodiment of an ECG system shaped for proper positioning of leads on a newborn. FIG. 8 shows chest strip 510 with leads individually wired into flexible printed circuit board 515 disposed in or on chest strip 510.

Chest strip 510 is shaped to conform to the anatomic positions of a newborn for the placement of the six precordial electrodes connected to leads (electrodes) (V1, V2, V3, V4, V5, and V6). RL electrode is positioned at the left lower corner of the strip (as viewed) to serve as the reference (ground) electrode. In this embodiment, three limb electrodes (RA, LA, LL) are connected to the chest strip by individual wires which run through chest strip 510 with six inches of extra wires outside the strip to connect to electrodes. The electrodes may be similar to electrodes described above (see FIG. 5). When the electrodes are detached from the chest strip, the RA, LA and LL electrodes can each be pulled to its respective anatomic position and still maintain a respective wire connection to the chest strip.

In this embodiment, chest strip 510 has three anatomic landmarks to assist proper electrode positioning; sternum mark 550 to place V1 and V2 electrodes on either side of the sternum, nipple line mark 555 for positioning V1 and V2 at the level of the $4^{th}$ intercostal space, and left nipple mark 558 above the V4 electrode to ensure that the chest strip is of appropriate size for the infant. The weight of 2-4 week old infants can vary, with the majority weighing 3 kg to 5 kg. To make the chest strip appropriate for newborns of various body sizes, the chest strip may be made in different sizes, e.g., one for newborns weighing approximately 2.5 kg to 4 kg and another for newborns weighing over 4 kg.

An upper or top surface of chest strip 510, in one embodiment, is covered by smooth fabric material with no exposed components. On the opposite or undersurface of chest strip 510 (intended to be in contact with the skin of a newborn), seven round shape electrodes, each 10 mm in diameter, are positioned in RL, V1, V2, V3, V4, V5, and V6 locations. The 10 mm electrodes contact surface is made of hydrogel adhesives. All chest and limb electrodes are connected to leads that are individually wired through chest strip 510 and connect to recorder module 525 on the right end (as viewed). In one embodiment, recorder module 525 is detachable from chest strip 510. Representatively, the leads in chest strip 510 terminate in a pin connection that mate or otherwise connect with terminals of recorder module 525. A snap on connector is designed to enable the connection of the wires from the chest strip to the recorder module. In one embodiment, the male connector of the snap on connector is at the chest strip and the female connector is at the recorder module. In one embodiment, the female connector at the recorder module is connected to an analog front end in the recorder module so that the analog signals from the chest strip are directed to the analog front end to be processed and converted to digital signals.

Figure 9:
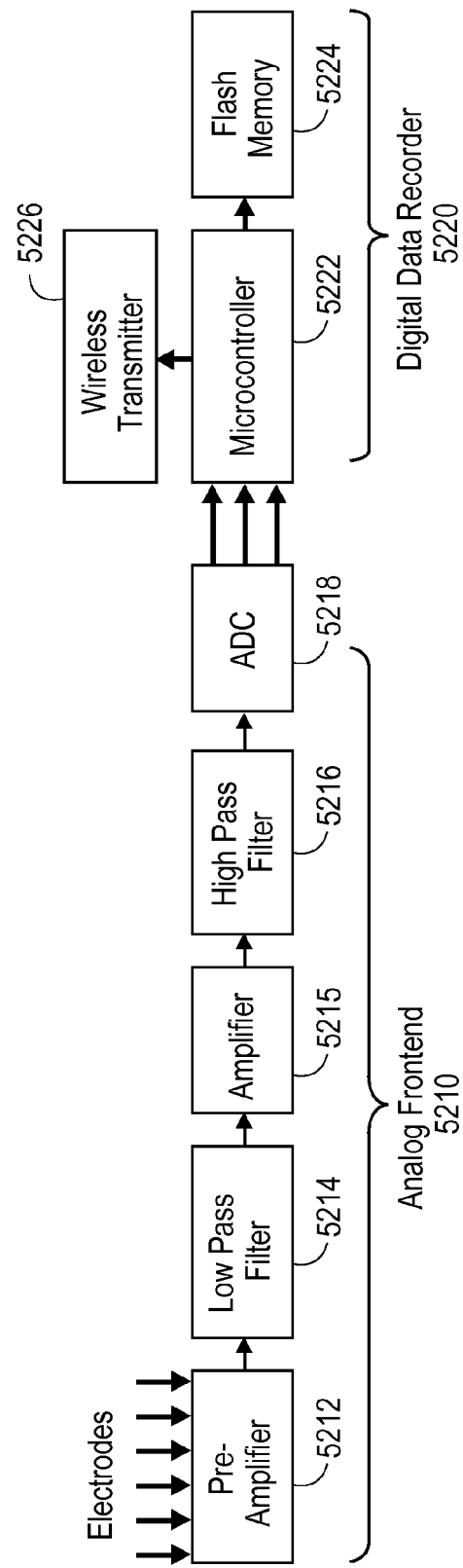
FIG. 9 shows a block diagram of components of a recorder module suitable for use with a chest strip.

Referring to FIG. 9 in one embodiment, recorder module 525 contains two components, analog front end 5210 and digital data recorder 5220. Representatively, analog front end 5210 includes: preamplifier 5212, low pass filter 5214, amplifier 5215, and high pass amplifier 5216. The analog front end receives the electrical signals collected from the leads/electrodes in chest strip 510 (e.g., signals from 10 leads/electrodes) and amplifies the signals to a suitable level (in mV) for signal processing. The bandpass filters are used to filter out the noise and select the frequency of interest at, for example, 0.04 Hz~150 Hz. After ECG signals are amplified and noise-filtered, the analog signals are converted to digital signals by the analog-to-digital converter (ADC) 5218.

In one embodiment, analog front end or receiver 5210 utilizes an ADS1298, a fully integrated analog front end chip for 12-lead ECG by Texas Instrument (TI). The ADS1298 has an integrated design on a single chip that is 12 millimeters (mm) by 12 mm by 0.8 mm, suitable to be accommodated on chest strip 510. ADS1298 is equipped with eight high-resolution, simultaneous sampling ADCs and integrated amplifier. The chip is also capable of digital pace detection and continuous lead-off detection.

Digital data recorder 5220 of recorder module 525 receives digital signals from analog front end 5210 (e.g., from ADC 5218) and, in one embodiment, writes the data on to a flash memory or sends the data to a wireless transmitter. The main components of digital data recorder 5220 include a microcontroller (MCU) 5222, flash memory 5224, wireless transmitter 5226, and a battery (not shown). MCU 5222 will regulate the data flow as well as manage the power. In one embodiment, the battery is a rechargeable Li-Polymer battery that will supply power for the entire detachable ECG Recorder Module. The default data flow function by MCU 5222 is to write the data to the flash memory. A mini-USB port may be placed for accessing the flash memory recording via a USB cable connecting to a processor (e.g., a computer). A user can switch the data to be directed to wireless transmitter 5226, which will send the data instantly. The transmitted data will be received by a wireless receiver connected to the processor.

Once chest strip 510 is placed on the infant, the analog front end 5210 will detect and ensure all electrodes have proper skin contact and signals. If there are leads off detected by ADS1298, a red signal light will be on. 12-Lead ECG data can be recorded continuously for many hours, until the flash memory is full, or until the battery power runs out. For the purpose of long QT syndrome screening, continuous ECG recording of 30 minutes typically results in adequate ECG data for reliable analysis. When the user finishes ECG data acquisition, in one embodiment, recorder module 525, may be detached (removed) from chest strip 510. In one embodiment, chest strip 510 is designed to be one-time use and will be disposed. The recorder module 525 can be transmitted (e.g., carried, mailed, etc.) by the user to a data center for ECG interpretation and data storage. Once any data on recorder module 525 is delivered to a data center by, for example, connecting recorder module 525 to the processor. Following any transmission, the data is transmitted to a processor at the data center, recorder module 525 may be sterilized, its battery recharged if necessary, and then the module can be attached to a new chest strip to be ready for use on the same or another infant.

Figure 10:
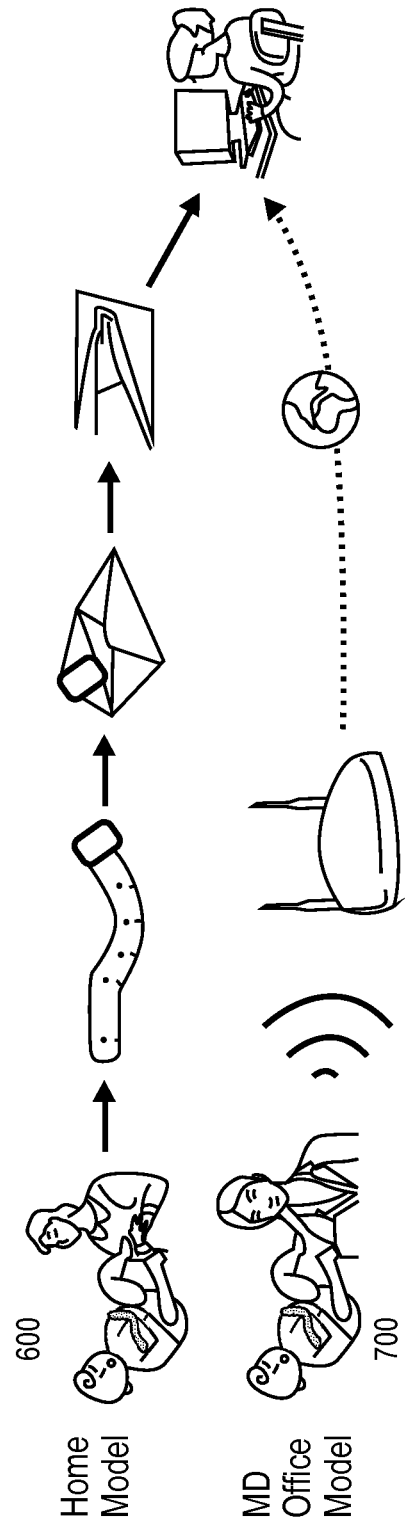
FIG. 10 shows two modes of operation of an ECG system.

FIG. 10 presents two modes of operation of the ECG systems described with reference to FIG. 8 and FIG. 9. In the first mode (identified by identifier 600), upon a baby's discharge after birth, the parents of the baby receive an ECG system from the hospital. When the baby is two to four weeks of age, the parents perform an ECG according to instructions. Once acquisition of ECG data is complete, the recorder module is detached and transported (e.g., mailed) to a central lab. At the central lab, the ECG data is retrieved and interpreted, and the recorder module is sanitized and recharged for reuse.

In the second mode of operation (identified by identifier 700), the ECG system is available at a pediatrician's office or other examination room. Representatively, at a baby's 2-week-old well childcare visit, a nurse places the device on the baby while taking vital signs. ECG data is continuously transmitted to a wireless receiver in the office for 30-60 minutes, until the baby is ready to go home. The wireless receiver can connect to a PC via a USB port, or to a router via an Ethernet port to forward the ECG data via the Internet to a secure server at a central lab. The recorder module will be sanitized at pediatrician's MD office for reuse on the next baby.

The ECG system described herein has many advantages over traditional ECG leads and cables. In particular, the ECG system described herein has a simple design that is easy to use, relatively error-proof, and compatible with current ECG machines. The ECG system described herein also minimizes skin contact on newborn thereby decreasing the risk for infection and/or skin reaction.

In the preceding detailed description, the invention is described with reference to specific exemplary embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. An apparatus comprising:
   a chest strip having dimensions suitable for a chest of a newborn and shaped to conform to anatomic positions of a newborn for a placement of precordial leads, the chest strip comprising (1) at least one landmark to aid in positioning of the chest strip on a newborn; (2) a plurality of precordial and limb leads for an electrocardiogram (ECG); and (3) an ECG data recorder coupled to the chest strip, wherein the ECG data recorder is configured to receive signals from the leads.

2. The apparatus of 1, wherein the precordial leads are positioned relative to the at least one landmark to correspond with a desired lead placement for a newborn.

3. The apparatus of claim 1, wherein the ECG data recorder is detachable.

4. The apparatus of claim 1, wherein the limb leads are connected to the chest strip by individual wires, the wires providing an acceptable length to extend a desired limb placement.

5. The apparatus of claim 1, further comprising a plurality of electrodes, wherein respective ones of the electrodes are coupled to the plurality of leads.

6. The apparatus of claim 3, further comprising an ECG analog receiver configured to receive analog data signals from the leads and convert the analog signals to digital signals for recording by the data recorder.

7. An apparatus comprising:
   a chest strip having dimensions suitable for a chest of a newborn, the chest strip and shaped to conform to anatomic positions of a newborn for a placement of precordial leads comprising (1) at least one landmark to aid in positioning of the chest strip on a newborn; (2) a plurality of precordial leads positioned to correspond with desired lead placement for an electrocardiogram (ECG); and (3) an ECG data recorder;
   a plurality of limb leads coupled to the chest strip,
   wherein the ECG data recorder is coupled to plurality of precordial leads and the plurality of limb leads and configured to receive electrocardiogram data generated by the plurality of precordial leads and the plurality of limb leads.

8. The apparatus of claim 7, wherein the ECG data recorder is detachable from the chest strip.

9. The apparatus of claim 7, further comprising a plurality of electrodes coupled to respective ones of the plurality of precordial leads.

10. The apparatus of claim 7, wherein the chest strip further comprise an analog receiver configured to receive analog data signals from the leads and convert the analog signals to digital signals for recording by the ECG data recorder.

11. The apparatus of claim 7, wherein the ECG data recorder is configured to record digital ECG data to onboard flash memory, and to send the ECG data to a wireless transmitter.

12. A method comprising:
   coupling a chest strip shaped to conform to anatomic positions of a newborn for a placement of precordial leads and comprising precordial leads and a data recorder to a newborn such that a V1 precordial lead is in a 4th intercostal space on a right sternal border and a V2 precordial lead will be in a 4th intercostal space on a left sternal border, the data recorder configured to receive electrocardiogram data from the precordial leads; and transmitting electrocardiogram data from the data recorder.

13. The method of claim 12, wherein the chest strip further comprises a plurality of limb leads, the method further comprising coupling the plurality of limb leads to respective ones of the limbs of the newborn.

14. The method of claim 12, wherein prior to transmitting electrocardiogram data, removing the data recorder from the chest strip.

15. The method of claim 14, wherein prior to transmitting electrocardiogram data, the method comprises:

retrieving electrocardiogram data.

16. The method of claim 15, wherein retrieving electrocardiogram data is done away from a medical office or examination room.

17. The method of claim 16, wherein after retrieving electrocardiogram data, detaching the data recorder from the chest strip.

18. The method of claim 12, wherein transmitting is done wirelessly.

* * * * *